US012171963B2

(12) United States Patent
Accisano, III

(10) Patent No.: US 12,171,963 B2
(45) Date of Patent: Dec. 24, 2024

(54) DRAINAGE CATHETER WITH SUTURE LUMEN

(71) Applicant: Merit Medical Systems, Inc., South Jordan, UT (US)

(72) Inventor: Nicholas Accisano, III, Howell, NJ (US)

(73) Assignee: Merit Medical Systems, Inc., South Jordan, UT (US)

( * ) Notice: Subject to any disclaimer, the term of this patent is extended or adjusted under 35 U.S.C. 154(b) by 11 days.

(21) Appl. No.: 16/854,510

(22) Filed: Apr. 21, 2020

(65) Prior Publication Data

US 2020/0338324 A1    Oct. 29, 2020

Related U.S. Application Data

(60) Provisional application No. 62/837,343, filed on Apr. 23, 2019.

(51) Int. Cl.
*A61M 27/00* (2006.01)
*A61M 25/02* (2006.01)

(52) U.S. Cl.
CPC ............ *A61M 27/00* (2013.01); *A61M 25/02* (2013.01); *A61M 2025/0286* (2013.01); *A61M 2205/32* (2013.01)

(58) Field of Classification Search
CPC .................. A61M 27/00; A61M 25/02; A61M 2025/0286; A61M 2025/0293; A61M 25/007
See application file for complete search history.

(56) References Cited

U.S. PATENT DOCUMENTS

| 5,308,318 A * | 5/1994 | Plassche, Jr. ......... A61M 27/00 604/540 |
| 5,439,006 A * | 8/1995 | Brennen ........... A61M 25/0136 604/95.04 |
| 9,427,378 B2 * | 8/2016 | Dziak ........................ C09J 5/04 |
| 10,792,467 B2 * | 10/2020 | Tran .................. A61M 25/0071 |
| 2004/0039339 A1 * | 2/2004 | Magnusson ........... A61M 25/04 604/523 |
| 2004/0059293 A1 * | 3/2004 | Chu ...................... A61M 25/04 604/107 |
| 2004/0181238 A1 * | 9/2004 | Zarbatany .......... A61B 17/0487 606/108 |

(Continued)

FOREIGN PATENT DOCUMENTS

WO    2009114811    9/2009

OTHER PUBLICATIONS

International Search Report and Written Opinion dated Jul. 29, 2020 for PCT/US2020/029125.

(Continued)

*Primary Examiner* — Benjamin J Klein
*Assistant Examiner* — Hans Kaliher
(74) *Attorney, Agent, or Firm* — Dorsey & Whitney LLP

(57) ABSTRACT

A drainage catheter configured for draining bodily fluid from a patient is disclosed. The drainage catheter may comprise a catheter tube with a drainage lumen and a suture lumen. A suture of the drainage catheter may be disposed within the suture lumen. The suture may be coupled to a distal end of the catheter tube and extend proximally through a hub disposed at the proximal end of the catheter tube.

14 Claims, 7 Drawing Sheets

(56) References Cited

U.S. PATENT DOCUMENTS

| | | | |
|---|---|---|---|
| 2006/0206096 A1* | 9/2006 | Accisano, III | A61M 25/0074 |
| | | | 604/540 |
| 2006/0217667 A1 | 9/2006 | Accisano et al. | |
| 2007/0032779 A1 | 2/2007 | Accisano et al. | |
| 2009/0182268 A1 | 7/2009 | Thielen et al. | |
| 2009/0247868 A1* | 10/2009 | Chesnin | A61M 25/0032 |
| | | | 604/523 |
| 2011/0054448 A1* | 3/2011 | Bourne | A61M 25/0068 |
| | | | 604/540 |
| 2011/0218520 A1 | 9/2011 | Andrich | |
| 2011/0295237 A1* | 12/2011 | Eells | A61M 25/0097 |
| | | | 604/540 |
| 2016/0045347 A1* | 2/2016 | Smouse | A61M 27/008 |
| | | | 623/23.66 |
| 2016/0192925 A1* | 7/2016 | Bachman | A61B 17/0401 |
| | | | 606/144 |
| 2016/0199625 A1* | 7/2016 | Rosenbaum | A61M 25/0071 |
| | | | 604/540 |
| 2018/0117288 A1 | 5/2018 | Lindsay et al. | |

OTHER PUBLICATIONS

Extended European Search Report dated May 2, 2023 for EP20794775.5.

* cited by examiner

DRAINAGE CATHETER WITH SUTURE LUMEN

RELATED APPLICATIONS

This application claims priority to U.S. Provisional Application No. 62/837,343, filed on Apr. 23, 2019 and titled "Drainage Catheter with Suture Lumen" which is hereby incorporated by reference in its entirety.

TECHNICAL FIELD

The present disclosure relates generally to elongate medical devices, including catheters. More particularly, some embodiments relate to drainage catheters comprising a drainage lumen and a suture lumen.

DETAILED DESCRIPTION

Figure 1:
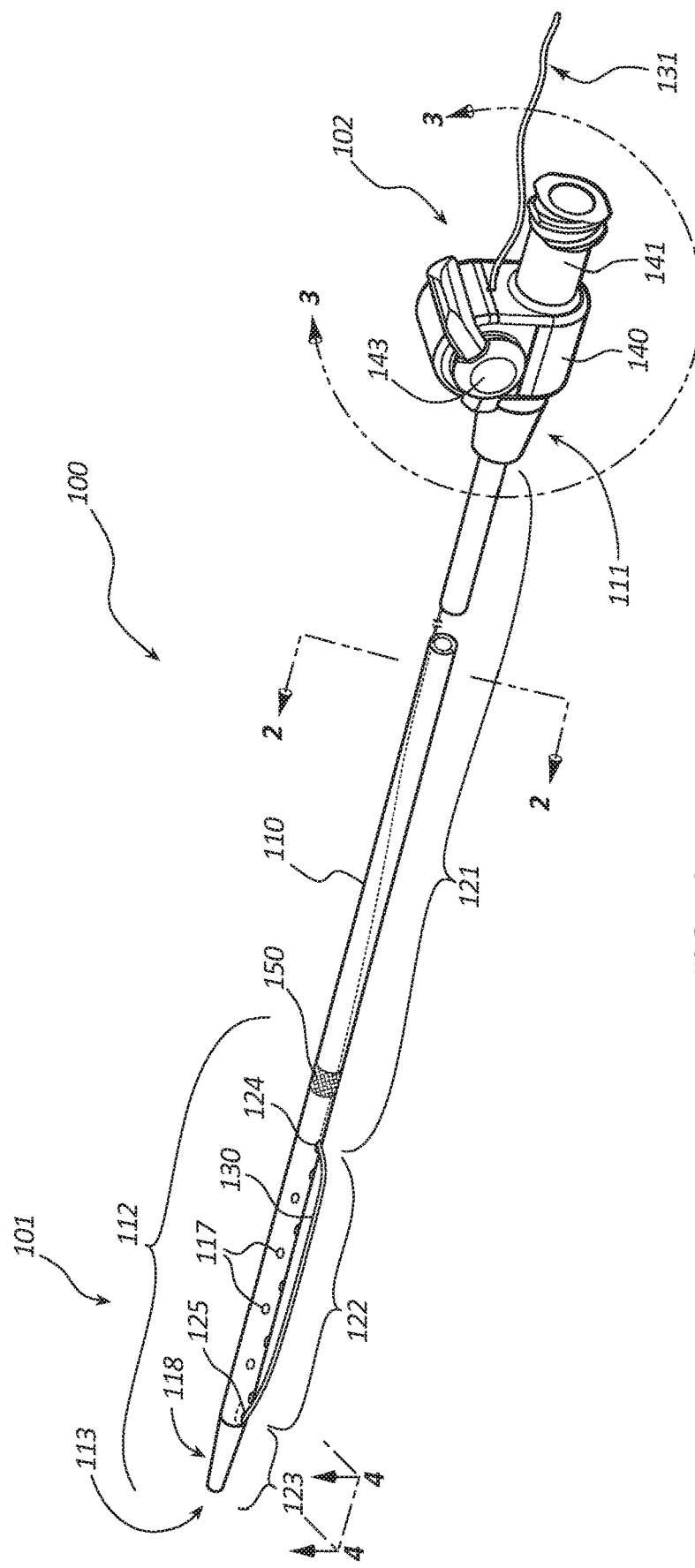
FIG. 1 is a perspective view of an embodiment of a drainage catheter shown in a first configuration.

Drainage catheters are used in a variety of medical settings for draining fluids from a patient's body. For example, a patient may suffer an injury or have a medical problem where a bodily tissue retains an excess amount of fluid, such as blood or other bodily serum. If the fluid is not removed further complications in the patient can occur such as rupturing or infection of the tissue. Accordingly, drainage catheters may be placed to remove these fluids from the patient, to either relieve pressure or otherwise ensure the fluid build-up does not result in tissue injury or other complications.

In some embodiments, drainage catheters may comprise a hub, an elongate catheter tube in fluid communication with the hub, and a distal portion. The catheter tube may include a plurality of drainage bores. The drainage bores may be configured to allow communication of fluid from the body through the elongate catheter tube. Some drainage catheters further include a suture disposed within a portion of the drainage lumen extending along the length of the catheter. The suture may be attached or secured to the tip of the catheter to facilitate deflecting the catheter tip away from a straight configuration into a curved or pig-tail configuration to anchor the catheter within a patient. For example, the practitioner may insert the catheter tube into a patient's body in a straight configuration, then pull on the suture to form a curved loop at the distal end to anchor the catheter within the body. Drainage catheters for various locations within the body, including drainage catheters for placement in the abdomen, chest, and other areas of the body are within the scope of this disclosure. Biliary and nephrostomy drainage catheters are likewise within the scope of this disclosure. Drainage catheters with drainage holes in various locations along the catheter, as well as drainage catheters with more than one pig-tail are also within the scope of the present disclosure.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities, including mechanical and fluidic interaction. Thus, two components may be coupled to each other even though they are not in direct contact with each other. The phrases "attached to" or "attached directly to" refer to interaction between two or more entities which are in direct contact with each other and/or are separated from each other only by a fastener of any suitable variety (e.g., mounting hardware or an adhesive). The phrase "fluid communication" is used in its ordinary sense and is broad enough to refer to arrangements in which a fluid (e.g., a gas or a liquid) can flow from one element to another element when the elements are in fluid communication with each other.

The terms "proximal" and "distal" are opposite directional terms. For example, the distal end of a device or component is the end of the component that is furthest from the practitioner during ordinary use. The proximal end refers to the opposite end, or the end nearest the practitioner during ordinary use. With specific application to drainage catheters, the proximal end refers to the end at which the hub is disposed, while the distal end is configured for insertion into a patient when in use.

As used herein, the term "suture" is broad enough to include filaments, tethers, wires, cords, straps, or other elongated flexible members configured to deflect or constrain a catheter when tension is applied to the suture.

In some embodiments, drainage catheters may comprise two or more lumens. For example, a drainage catheter may comprise a drainage lumen and a suture lumen. In such catheters, a suture configured to deflect a portion of the catheter may be disposed within a suture lumen and the drainage lumen may be dedicated to fluid flow. As compared to devices wherein a suture is simply disposed within the drainage lumen, use of a suture lumen may tend to facilitate flow through the drainage catheter. For example, the presence of a suture within a drainage lumen may affect flow of fluid through the drainage lumen by creating a reduction in flow area, or the suture may interfere with flow of solid or semi-solid particles in the fluid as they may become entangled with the suture. Additionally, in some applications, fluid to be drained may contain elements prone to precipitation onto internal surfaces, and the suture creates additional surface area upon which precipitation may build up. Precipitation build-up on the suture may also inhibit displacement of the suture and inhibit relaxation of the curved distal end when the procedure is complete. A suture in the drainage lumen may also interfere with a straightening device, such as a stylet, preventing its insertion into or removal from the drainage lumen.

Figure 2:
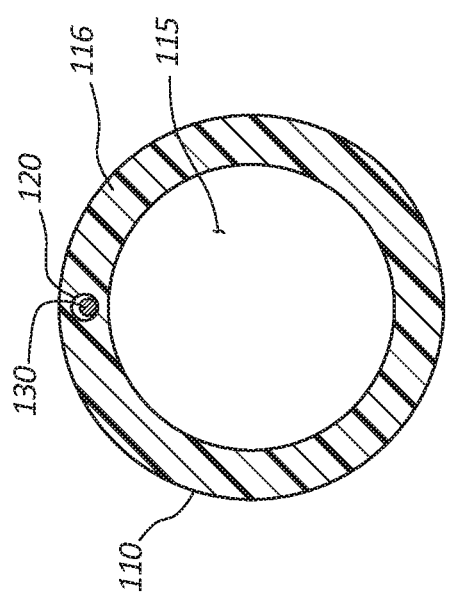
FIG. 2 is a cross-sectional end view of a catheter tube of the drainage catheter of FIG. 1.

FIGS. 1-5 illustrate a drainage catheter 100 and related components. FIG. 1 is a perspective view of the drainage catheter 100 and FIG. 2 is a cross-sectional view of a catheter tube 110 of the drainage catheter 100, taken through plane 2-2 of FIG. 1. The drainage catheter 100 may be used to provide a fluid pathway for draining bodily fluid from a cavity or tissue of a patient. A distal portion 101 of the drainage catheter 100 may be configured to be inserted into the patient while a proximal end 102 remains external to the patient. The drainage catheter 100 may be coupled to a fluid transfer device (not shown) to facilitate removal of excess fluid from a defined location within the patient. The distal portion 101 may be selectively disposed in an anchor configuration to provide for retention of the distal portion 101 within the patient as further described below. Optional secondary devices such as stylets, trocars, etc. may be used in conjunction with the drainage catheter 100 to facilitate insertion and placement of the distal portion 101 within the patient. In the illustrated embodiment, the drainage catheter 100 includes an elongate catheter tube 110, a suture 130 extending along the catheter tube 110, and a catheter hub 140 coupled to a proximal end 111 of the catheter tube 110.

The catheter tube 110 includes a drainage lumen 115 comprising an annular wall 116 extending the length of the catheter tube 110. The catheter tube 110 may be formed of a flexible or semi-flexible bio-compatible material. The catheter tube 110 may be sufficiently flexible to enable the drainage catheter 100 to navigate various anatomical locations within a patient. Further, the catheter tube 110 may be configured in a preformed shape in the absence of an external or internal force. The preformed shape may include straight portions and curved portions. In some embodiments the outside surface of the catheter tube 110 may be cylindrical. In other embodiments, the outside surface may have a shape other than cylindrical, for example, oval or polygonal. The drainage lumen 115 may be defined so as to maximize a cross-sectional area for fluid flow. In some embodiments, the drainage lumen 115 may comprise a circular cross section.

The catheter tube 110 may include a distal tip 118. The distal tip 118 may be shaped and sized to facilitate insertion of a distal portion 112 of the catheter tube 110 into the patient. In some embodiments, the distal tip 118 may include an external taper 119. The catheter tube 110 may include an opening at a distal end 113 of the catheter tube 110 or the distal end 113 of the catheter tube 110 may be closed. In some embodiments, the drainage lumen 115 may be sized or otherwise configured to receive a stiffening member therethrough, such as a stylet or a needle.

The catheter tube 110 may comprise one or more drainage ports 117. In the illustrated embodiment, the catheter tube 110 comprises a plurality of drainage ports 117 disposed along a distal portion 112 of the catheter tube 110. Each of the drainage ports 117 comprises an orifice extending through the annular wall 116 of the catheter tube 110, providing fluid communication between an outside environment and the drainage lumen 115. The drainage ports 117 may thus be configured to provide for the passage of fluid between an anatomical location to be drained and the drainage lumen 115. The drainage ports 117 may be positioned along the catheter tube 110 such that when the distal portion 101 of the drainage catheter 100 is placed at the desired location within a patient, the drainage ports 117 are in fluid communication with the fluid to be removed from the patient.

The drainage ports 117 may be sized to facilitate fluid flow depending on the application or characteristics of a procedure. In some embodiments, the aperture size of the drainage ports 117 may be substantially similar to the drainage lumen 115. In other embodiments, the size of the drainage ports 117 may be smaller or larger than the drainage lumen 115. The drainage ports 117 may be disposed on a single side of the catheter tube 110, or they may be distributed around the catheter tube 110. In some embodiments, the drainage ports 117 may be disposed along the inside of a curved portion of the catheter tube 110. Such placement may inhibit blockage of one or more drainage ports 117 by adjacent internal patient tissue.

In the illustrated embodiment, the catheter hub 140 is coupled to the proximal end 111 of the catheter tube 110. The catheter hub 140 is configured to provide for fluid communication between the drainage lumen 115 and a fluid transfer device, for example, a syringe or a drainage bag. The catheter hub 140 may include a fluid connector 141 to facilitate coupling to the fluid transfer device. In some embodiments, the fluid connector 141 may be a female or male Luer connector.

As shown in FIGS. 1 and 2 the drainage catheter 100 may comprise a suture lumen 120 extending along at least a portion of the catheter tube 110. The suture lumen 120 may extend along the entire length of the catheter tube 110. In some embodiments, the suture lumen 120 may not be continuous along the entire length of the catheter tube 110. In other words, the suture lumen 120 may be extend only along one or more portions of the catheter tube 110. The suture lumen 120 may be sized to provide for passage of a suture therethrough. The suture lumen 120 may be disposed within the annular wall 116 of the catheter tube 110.

In some embodiments, the suture lumen 120 and the drainage ports 117 may be arranged along the catheter tube 110 such that they do not intersect. In other embodiments, the suture lumen 120 may intersect with one or more drainage ports 117. Still in other embodiments, the suture lumen 120 may intersect with all drainage ports 117. Thus, the suture lumen 120 may or may not be in communication with the drainage ports 117.

For purposes of description, the suture lumen 120 may be understood as defining a proximal region 121, a central region 122, and a distal region 123. The proximal region 121 may comprise a continuous length of the suture lumen 120 extending distally from the proximal end 111 of the catheter tube 110 to an exit port 124. The exit port 124 comprises an aperture extending between the suture lumen 120 and the exterior surface of the annular wall 116 and is configured for passage of the suture 130 therethrough. In some embodiments, the exit port 124 may also extend inward and intersect the drainage lumen 115. In some embodiments, the exit port 124 may be one of the drainage ports 117.

The distal region 123 of the suture lumen 120 extends proximally from the distal end 113 of the catheter tube 110 to an entrance port 125. Similar to the exit port 124, the entrance port 125 comprises an aperture extending between the suture lumen 120 and the exterior surface of the annular wall 116 and is configured for passage of the suture 130 therethrough. In some embodiments, the entrance port 125 may also intersect the drainage lumen 115 and may also be one of the drainage ports 117. The central region 122 is defined as the length segment of the suture lumen 120 extending between the exit port 124 and the entrance port 125. In the illustrated embodiment, the drainage ports 117 are shown disposed between the exit port 124 and the entrance port 125, i.e., along the central region 122. However, one or more drainage ports 117 may be disposed proximal of the exit port 124 and/or distal of the entrance port 125.

Figure 3:
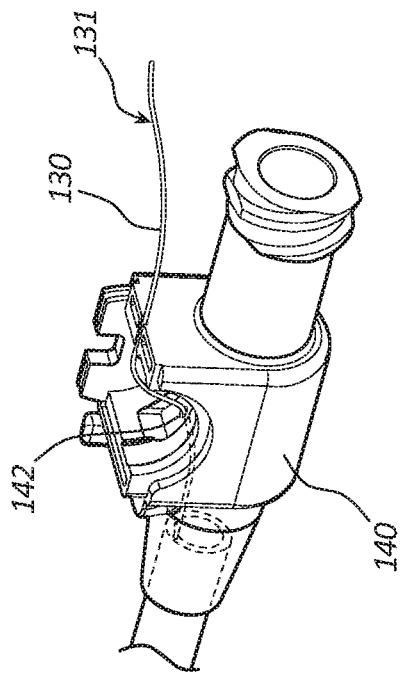
FIG. 3 is a detail view of a portion of a catheter hub of the drainage catheter of FIG. 1.

FIG. 3 is a detail view of a portion of the catheter hub 140 coupled to the proximal end 111 of the catheter tube 110. As shown in FIG. 3, the catheter hub 140 includes a suture passageway 142. The suture passageway 142 is configured for longitudinal passage of the suture 130 through the catheter hub 140. The suture passageway 142 may be positioned such that upon coupling of the catheter hub 140 with the catheter tube 110, the suture passageway 142 is aligned with the suture lumen 120. As such, the suture passageway 142 may be understood as a proximal extension of the suture lumen 120 toward the proximal end 102 of the drainage catheter 100.

The suture 130 may be formed of any suitable material to provide tension. In some embodiments, the suture 130 may be of a suture construction so as to provide tension with a minimal cross section. In some embodiments, the suture 130 may have a guidewire formation so that the suture 130 may be longitudinally displaced by being pushed from the proximal end 131 or the distal end 132. The suture may be formed of a thermoplastic material to accommodate the shape formation with applied energy such as heat or ultrasonic energy. The suture 130 may comprise a material or surface treatment or coating to facilitate reduced friction within the suture lumen 120. The suture 130 may be formed of a biocompatible material or treated to be biocompatible. The suture 130 may also be formed of a material compatible with bonding to the catheter tube 110.

The suture 130 may be coupled to the catheter tube 110 such that tension on the suture 130, or displacement of a portion of the suture 130 relative to the catheter tube 110, may affect the shape or curvature of the catheter tube 110. For example, tension in the suture 130 may inhibit at least a portion of the catheter tube 110 from being deflected one or more directions by an external force, for example, through contact of the catheter tube 110 with internal portions of the patient. More specifically, tension in the suture 130 may constrain a first location of the catheter tube 110 and a second location of the catheter tube 110 to be within a defined proximity relative to each other. For example, tension on the suture 130 may tend to pull the entrance port 125 into proximity with the exit port 124, which also results in the distal portion 112 of the catheter tube 110 assuming a curved or pigtail configuration.

As described in different terms, tension on, or displacement of, the suture 130 relative to a portion of the catheter tube 110 may cause a curvature of at least a portion of the catheter tube 110 away from a first radius of curvature toward a second radius of curvature, wherein the second radius of curvature is less than the first radius of curvature. In some instance, the external forces acting upon the catheter tube 110 when inserted into a patient may cause a portion of the catheter tube 110 to assume a first shape. In such an instance, displacement of the suture 130 may cause the portion of the catheter tube 110 to assume a second shape different from the first shape.

The suture 130 may be disposed within at least a portion of the suture lumen 120. In the illustrated embodiment, the suture 130 is disposed within and slidably coupled to the proximal region 121 of the suture lumen 120 and the suture passageway 142 of the catheter hub 140. In some embodiments, a free proximal end 131 of the suture 130 may extend proximally away from the catheter hub 140. The suture 130 may exit the suture lumen 120 through the exit port 124 and extend distally along the central region 122 external to the catheter tube 110.

The suture 130 may re-enter the suture lumen 120 through the entrance port 125 and be disposed within the suture lumen 120 along at least a portion of the distal region 123. In some embodiments, the suture 130 may be disposed within the suture lumen 120 along the complete length or substantially along the complete length of the distal region 123. The suture 130 may be coupled to the catheter tube 110 within the distal region 123 of the suture lumen 120 such that displacement of the suture 130 within the distal region 123 is inhibited. In some embodiments, a distal end 132 of the suture 130 may be disposed within the suture lumen 120 along the distal region 123.

Tension on, or proximal displacement of, a portion of the suture 130 through the suture passageway 142 may draw the entrance port 125 toward the exit port 124 and/or otherwise change the shape or curvature of the catheter tube 110. For example, proximal displacement of the suture 130 adjacent the exit port 124 may cause deflection of the central region 122 of the catheter tube 110. In some instances, proximal displacement of the suture 130 may cause a segment of the catheter tube 110 adjacent the entrance port 125 to contact a segment of the catheter tube 110 adjacent the exit port 124. Similarly, tension in the suture 130 may prevent the entrance port 125 from being displaced away from the exit port 124 by a force applied to the catheter tube 110 such as, by a force applied to the distal portion 112 of the catheter tube 110. In some instances, while the drainage catheter 100 is disposed within a patient, forces may be applied to the catheter hub 140 tending to the draw the drainage catheter 100 out of the patient, and thus causing internal portions of the patient to apply a reaction force to the distal portion 112 of the drainage catheter tube 110.

The catheter hub 140 may include a suture lock 143. The suture lock 143 may provide for selective prevention and allowance of displacement of the suture 130 along the suture passageway 142. The suture lock 143 may be disposed in a release configuration such that upon tension applied to the suture 130, the suture 130 may be displaced through the suture passageway 142. Similarly, the suture lock 143 may be disposed in a secure configuration such that upon tension applied to the suture 130, displacement of the suture 130 through the suture passageway 142 is inhibited. In some embodiments, the suture lock 143, when in the secure configuration, may inhibit displacement of the suture 130 through the suture passageway 142 in a single direction, for example, in the distal direction.

Figure 4:
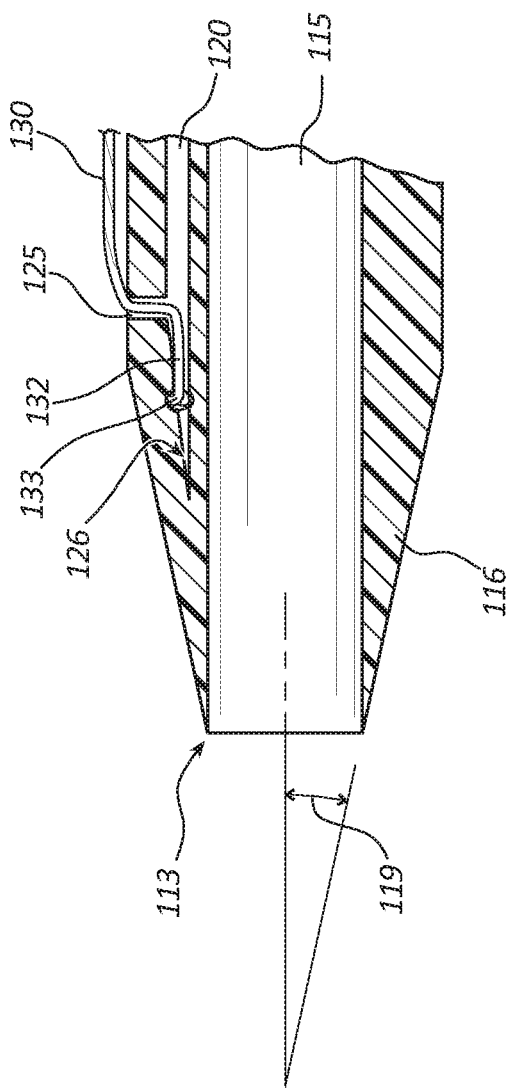
FIG. 4 is a cross-sectional side view of a distal portion of the drainage catheter of FIG. 1.

FIG. 4 is a cross-sectional side view of a distal portion of the catheter tube 110. FIG. 4 shows the drainage lumen 115 and the suture lumen 120 adjacent the distal tip 118 of the illustrated embodiment. Also shown is the distal end 132 of the suture 130 disposed within the suture lumen 120. In some embodiments, the suture 130 may be coupled to an internal surface of the suture lumen 120. In some embodiments, a portion of the suture 130 may be bonded to a portion of the distal region 123 of the suture lumen 120 with an adhesive. In some embodiments, the distal end 132 of the suture 130 may include an attachment segment 133. The attachment segment 133 may include a surface treatment to enhance coupling, for example, an etched surface or a textured surface. The attachment segment 133 may also include a knot, a series of knots, a bulbous portion, a sleeve, or any other suitable coupling enhancement feature. In some embodiments, the shape of the suture lumen 120 may be altered to secure the distal end 132 of the suture 130 within the distal region 123. Further, the shape of the suture lumen 120 may be altered by the application of energy applied to the external surface of the catheter tube 110, for example, heat or ultra-sonic energy. In some embodiments, the process of forming the external taper 119 of the distal tip 118 may simultaneously secure the distal end 132 of the suture 130 within the distal region 123 of the suture lumen 120. For example, the external taper 119 may be formed by heating and compressing the distal tip 118 of the catheter tube 110. This heat and compression may also cause the suture lumen 120 to compress around, and secure, the distal end 132 and/or the attachment segment 133 of the suture 130. In some embodiments, alteration of the shape of the suture lumen 120 may form a closed end 126 of the suture lumen 120 within the distal region 123 of the suture lumen 120.

Figure 5:
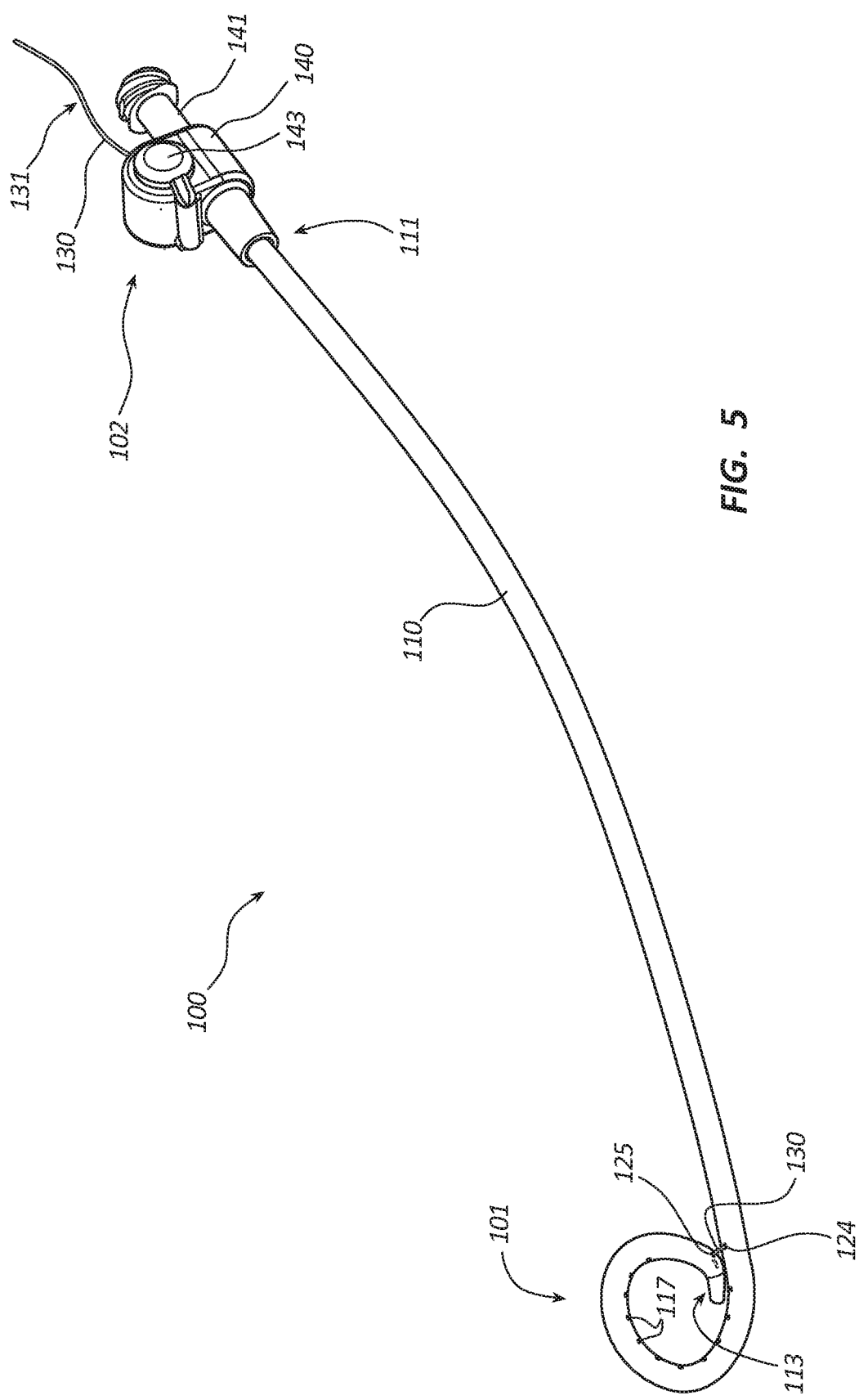
FIG. 5 is a perspective view of the drainage catheter of FIG. 1 shown in a second configuration.

FIG. 5 is a perspective view of the drainage catheter 100 in a second or an anchor configuration. This may be compared to the perspective view of a first or a straight configuration shown in FIG. 1. The anchor configuration may be defined as any shape or combination of shapes configured to inhibit the distal portion 112 of the catheter tube 110 from being dislodged from the patient or withdrawn from the patient along the catheter insertion path. In some embodiments, the anchor configuration may comprise a first segment of the catheter tube 110 constrained at an angle relative to a second segment of the catheter tube 110. In some embodiments, the anchor configuration may comprise a first segment of the catheter tube 110 constrained to be within a defined distance from a second segment of the catheter tube 110. Tension in the suture 130 may constrain the drainage catheter 100 in the anchor configuration and thus tend to maintain the position of the drainage catheter 100 in the anchor configuration. The suture lock 143 may prevent distal displacement of the suture 130 so as to constrain the drainage catheter 100 in the anchor configuration. In the illustrated embodiment, the suture 130 is proximally displaced such that the entrance port 125 is constrained to be adjacent the exit port 124 causing a loop to be formed in the distal portion 112 and thus dispose the drainage catheter 100 in the anchor configuration.

In some embodiments, the catheter tube 110 may be pre-formed toward a non-anchor configuration. In other words, the catheter tube 110 may be pre-formed to be relatively straight as shown in FIG. 1. A straight preform may be desirable to provide ease in placing a straight stylet (not shown) in the drainage lumen 115 to facilitate insertion of the drainage catheter 100 into the patient. In some embodiments, the catheter tube 110 may be pre-formed toward the anchor configuration. The catheter tube 110 may be pre-formed to include at least one loop using heat to set the catheter tube 110 in the anchor configuration when the catheter tube 110 is not constrained. The catheter tube 110 may be formed of any suitable heat-settable material, such as polyethylene, polypropylene, polyurethane, polyvinyl chloride, polyamide, etc. Alternatively, the tube 110 may include shape memory inserts (e.g. nitinol) that have been pre-formed into a loop shape. In some pre-formed embodiments, a straight cylindrical sleeve (not shown) may be used to slide over the curved portion of the catheter tube 110 to straighten the curved portion prior to inserting the stylet. Even in embodiments wherein the drainage catheter 100 is pre-formed toward the anchor configuration, tension on the suture 130 may be configured to maintain the drainage catheter in the anchor configuration.

The drainage catheter 100 may include one or more radiopaque markers 150 disposed along the catheter tube 110 to facilitate visibility of the drainage catheter 100 while the drainage catheter 100 is inserted into a patient. In some embodiments, the radiopaque markers 150 may indicate the shape of the distal portion 112 of the catheter tube 110 and/or indicate whether or not the drainage catheter 100 is disposed in the anchor configuration.

Figure 7:
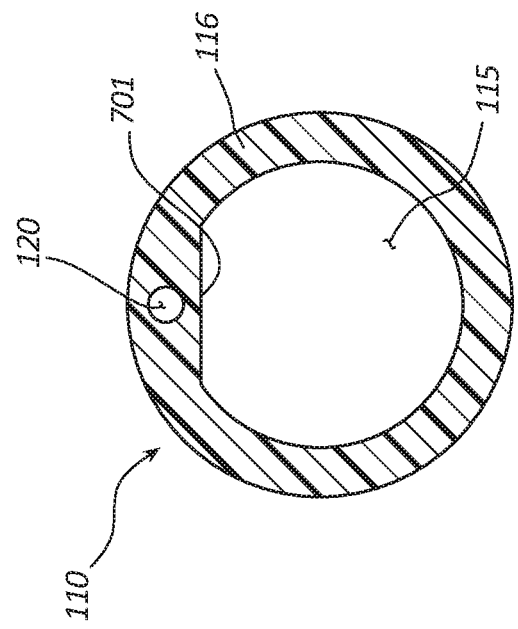
FIG. 7 is a cross-sectional end view of another embodiment of a catheter tube.
Figure 6:
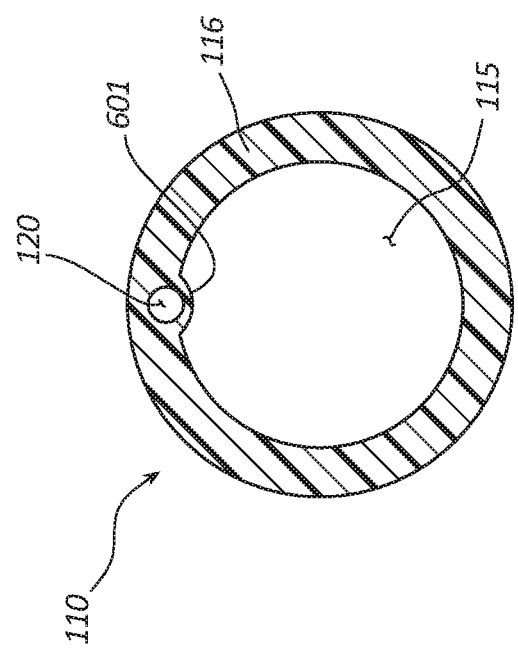
FIG. 6 is a cross-sectional end view of another embodiment of a catheter tube.

FIGS. 6 and 7 show alternative embodiments of the catheter tube 110 showing alternative configurations of the suture lumen 120 and the drainage lumen 115. For convenience the catheter tube 110, drainage lumen 115, annular wall 116, and suture lumen 120 are shown in these alternatives using the same number scheme as the embodiment of FIGS. 1-5. FIG. 6 shows a protrusion 601 extending inward along an inner surface of the annular wall 116. The protrusion 601 may be configured to provide a thicker portion of the annular wall to accommodate the suture lumen 120 while also allowing for a thinner annular wall 116 around the remainder of the catheter tube 110. The alternative of FIG. 6 may thus allow a relatively larger cross-sectional area of the drainage lumen 115 while keeping the same outside diameter and circular shape of the catheter tube 110 when compared to the embodiment of FIGS. 1-5. FIG. 7 shows another alternative embodiment wherein a protrusion 701 is defined by a D-shaped cross-section of the drainage lumen 115, again creating a thicker portion of the annular wall to accommodate the suture lumen 120. Each of the illustrated embodiments comprise a circular outside diameter of the catheter tube 110. This geometry may be configured to mate with a cylindrical sleeve configured to straighten the catheter tube 110 during use. Other embodiments may comprise features (ridges, protrusions, etc.) on the outside diameter of the catheter tube 110. Some such embodiments may be configured to mate with a cylindrical stylet to be disposed within the drainage lumen 115 to straighten the catheter tube 110.

A method of use of the drainage catheter 100 may comprise one or more of the following operational steps. The practitioner may initially dispose the suture lock 143 in a release configuration to allow the suture 130 to be displaced within the suture lumen 120. With the suture lock 143 in the release configuration, the practitioner may manipulate the distal portion 112 of the catheter tube 110 into a straight configuration, i.e., a non-anchor configuration. The practitioner may insert a stylet in the drainage lumen 115 to establish a substantially straight configuration and to provide enhanced stiffness to the catheter tube 110. In some instances, the practitioner may initially slide a cylindrical sleeve over the outside of the distal portion 112 to straighten the distal portion 112 prior to inserting a stylet or needle. The practitioner may then insert the distal portion 112 of the catheter tube 110 into the patient positioning the distal portion 112 at a desired location for the removal of fluid. The practitioner may utilize X-ray or other scanning devices to visualize one or more radiopaque markers 150 during the placement of the drainage catheter 100. The practitioner may displace the suture 130 proximally by manually pulling on the proximal end 131 to urge the drainage catheter 100 into the anchor configuration. The suture lock 143 may be used to maintain tension on, and the position of, the suture 130 to maintain the drainage catheter 100 in the anchor configuration. A fluid transfer device may be coupled to the catheter hub 140 to collect flow out of the patient. To remove the drainage catheter 100, the practitioner may dispose the suture lock 143 into the release configuration allowing the suture 130 to slidably displace within the suture lumen 120 and thereby allow the distal portion 112 of the catheter tube 110 to be manipulated away from the anchor configuration.

The practitioner may then draw the drainage catheter 100 out of the patient while allowing the distal tip 118 to displace the suture 130 distally within the suture lumen 120 as the distal portion 112 is disposed away from the anchor configuration.

Figure 8:
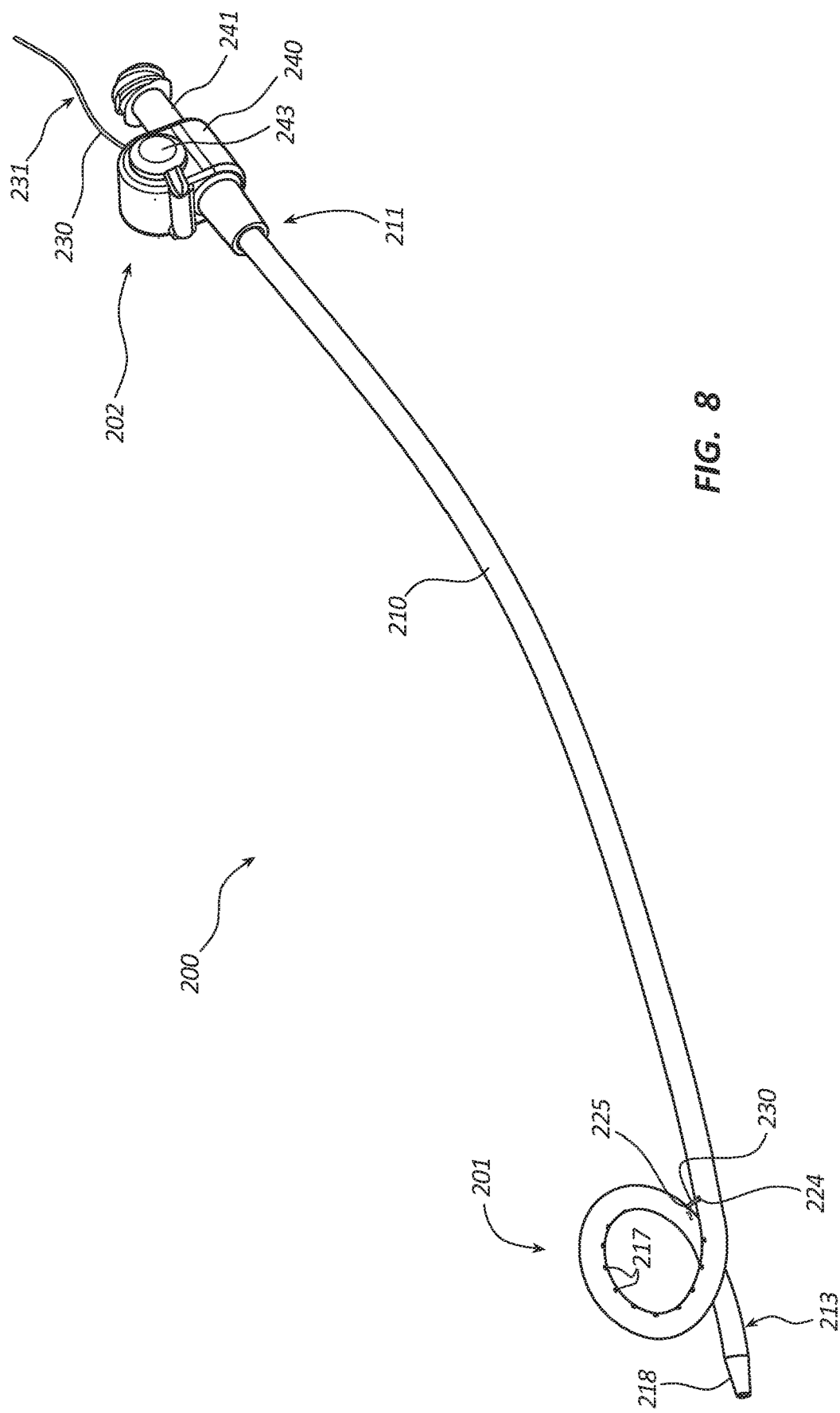
FIG. 8 is a perspective view of another embodiment of a drainage catheter in a second configuration.

FIG. 8 depicts an embodiment of a drainage catheter 200 that resembles the drainage catheter 100 described above in certain respects. Accordingly, like features are designated with like reference numerals, with the leading digit incremented to "2." For example, the embodiment depicted in FIG. 8 includes a catheter tube 210 that may, in some respects, resemble the catheter tube 110 of FIG. 1. Relevant disclosure set forth above regarding similarly identified features thus may not be repeated hereafter. Moreover, specific features of the drainage catheter 100 and related components shown in FIGS. 1-7 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the drainage catheter 200 and related components depicted in FIG. 8. Any suitable combination of the features, and variations of the same, described with respect to the drainage catheter 100 and related components illustrated in FIGS. 1-7 can be employed with the drainage catheter 200 and related components of FIG. 8, and vice versa. This pattern of disclosure applies equally to further embodiments depicted in subsequent figures and described hereafter, wherein the leading digits may be further incremented.

FIG. 8 is a perspective view of an embodiment of a drainage catheter 200 in an anchor configuration. As with the drainage catheter 100 of FIGS. 1-7, the drainage catheter 200 of FIG. 8 may be disposed in a first or straight configuration (analogous to the straight configuration of the drainage catheter 100 as shown in FIG. 1) or in a second or anchor configuration such as shown in FIG. 8. As depicted, the drainage catheter 200 can include a catheter tube 210 having a distal end 213 and a proximal end 211, a catheter hub 240 coupled to the proximal end 211, and a suture 230 extending along the catheter tube 210 and extending proximally from the catheter hub 240. A distal tip 218 is shown coupled to the distal end 213. The suture 230 can be operably coupled to a distal portion 201 of the catheter tube 210 as previously described with a portion of the suture 230 extending externally of the tube 210 between an exit port 224 and an entrance port 225. In the anchor configuration, tension can be applied to the suture 230 causing a loop to be formed adjacent the distal portion 201 such that the distal end 213 and the distal tip 218 extends distally from the loop. Thus, as compared to the drainage catheter 100 of FIGS. 1-7, the drainage catheter 200 of FIG. 8 may be configured such that the distal end 213 extends distally from the loop rather than being disposed within the loop as shown in FIG. 5. Catheters wherein the distal end extends a variety of lengths beyond the loop are within the scope of this disclosure, including embodiments where it extends from 1 to 4 inches, from 1 to 2 inches, about 1 inch, and so forth. Furthermore, embodiments wherein the distal end 213 extends such that the loop is closer to the proximal end 211 than the distal end 213 are also within the scope of this disclosure (including, for example, the embodiment described in connection with FIG. 10). The distal portion 201 may include a plurality of drainage ports 217. In some embodiments, when the drainage catheter 200 is in the anchor configuration, the drainage ports 217 may be disposed adjacent the loop.

Figure 9:
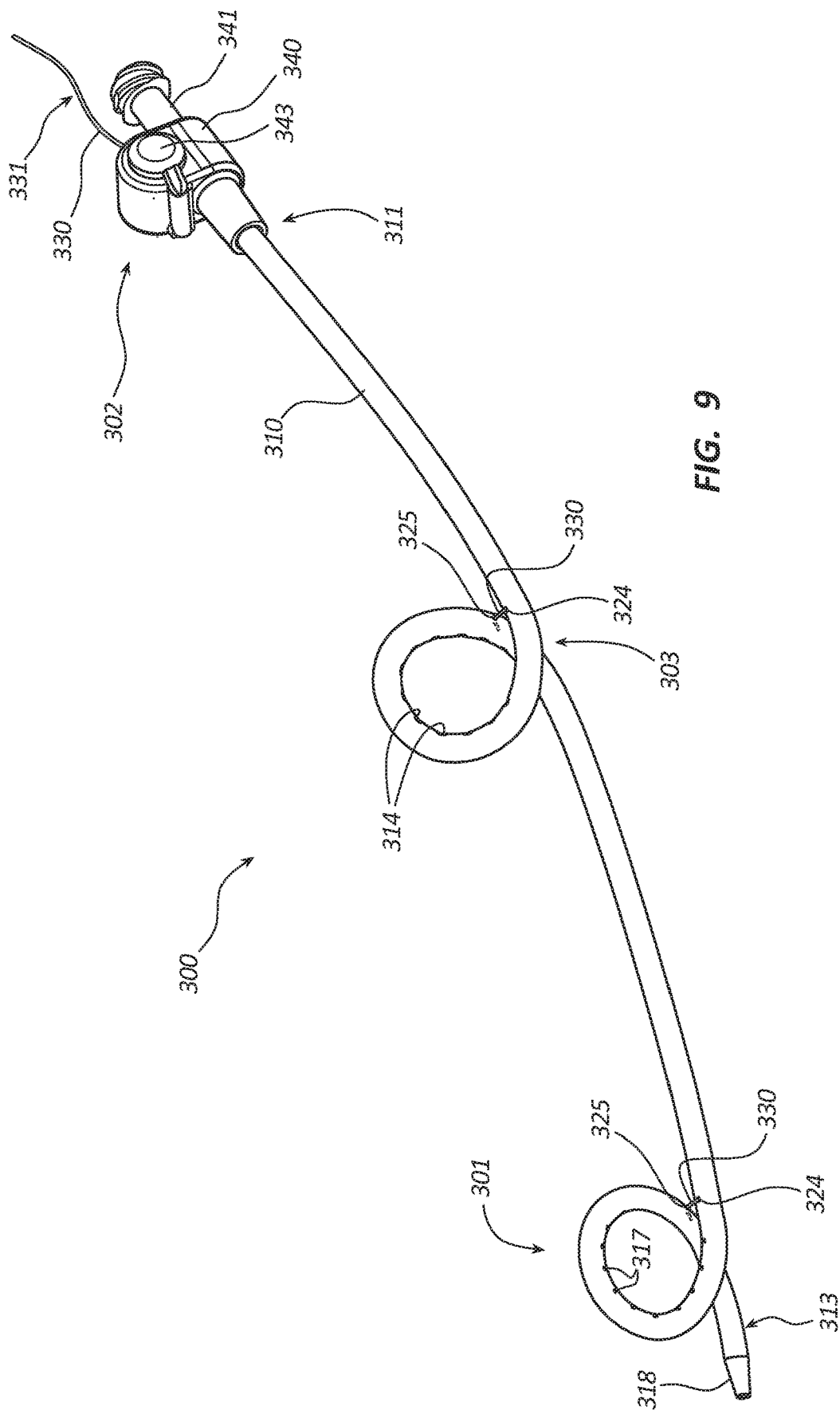
FIG. 9 is a perspective view of another embodiment of a drainage catheter in a second configuration.

FIG. 9 is a perspective view of an embodiment of a drainage catheter 300 in an anchor configuration. As with the drainage catheter 100 of FIGS. 1-7, the drainage catheter 300 of FIG. 9 may be disposed in a first or straight configuration (analogous to the straight configuration of the drainage catheter 100 as shown in FIG. 1) or in a second or anchor configuration such as shown in FIG. 9. As depicted the drainage catheter 300 can include a catheter tube 310 having a distal end 313 and a proximal end 311, a catheter hub 340 coupled to the proximal end 302, and a suture 330 extending along the catheter tube 310 and extending proximally from the catheter hub 340. A distal tip 318 is shown coupled to the distal end 313. The suture 330 can be operably coupled to a distal portion 301 of the catheter tube 310 as previously described with a portion of the suture 330 extending externally of the tube 310 between an exit port 324 and an entrance port 325. In the anchor configuration, tension can be applied to the suture 330 causing a distal or first loop to be formed adjacent the distal portion 301 such that the distal end 313 and the distal tip 318 extend distally from the distal loop (analogous to, for example, the distal portion of the embodiment of FIG. 8). Alternatively, the distal end 313 and the distal tip 318 can be enclosed within the distal loop (analogous to, for example, the distal portion of the embodiment of FIG. 5). The distal portion 301 can include a plurality of drainage ports 317. When the drainage catheter 300 is in the anchor configuration, the drainage ports 317 can be disposed adjacent the distal loop.

FIG. 9 further depicts a proximal or second loop disposed adjacent a middle portion 303 of the catheter tube 310. In the anchor configuration, as illustrated in FIG. 9, tension can be applied to the suture 330 causing the proximal loop to be formed such that the distal portion 301 extends distally from the proximal loop. The suture 330 can extend through the proximal portion 303 and be operably coupled to the middle portion 303 with a portion of the suture 330 extending externally of the tube 310 between an exit port 327 and an entrance port 328. The distal loop and the proximal loop may be formed substantially simultaneously when tension is applied to the suture 330.

In another embodiment, a first suture 330 can be operably coupled to the distal portion 301 and to a first suture lock 143 to facilitate forming of the distal loop and a second suture can be operably coupled to the middle portion 303 and to a second suture lock to facilitate forming of the proximal loop. The first and second sutures can be either disposed in a common suture lumen or in separate suture lumens. Further, a single suture lock 143 may be used to lock both sutures simultaneously or independently or a separate suture lock may be used in connection with the second suture. In some embodiments, the distal loop and the proximal loop can be formed sequentially when tension is applied to the first and second sutures sequentially. The middle portion 303 can include a plurality of drainage ports 314. When the drainage catheter 300 is in the anchor configuration, the drainage ports 314 can be disposed adjacent the proximal loop.

Figure 10:
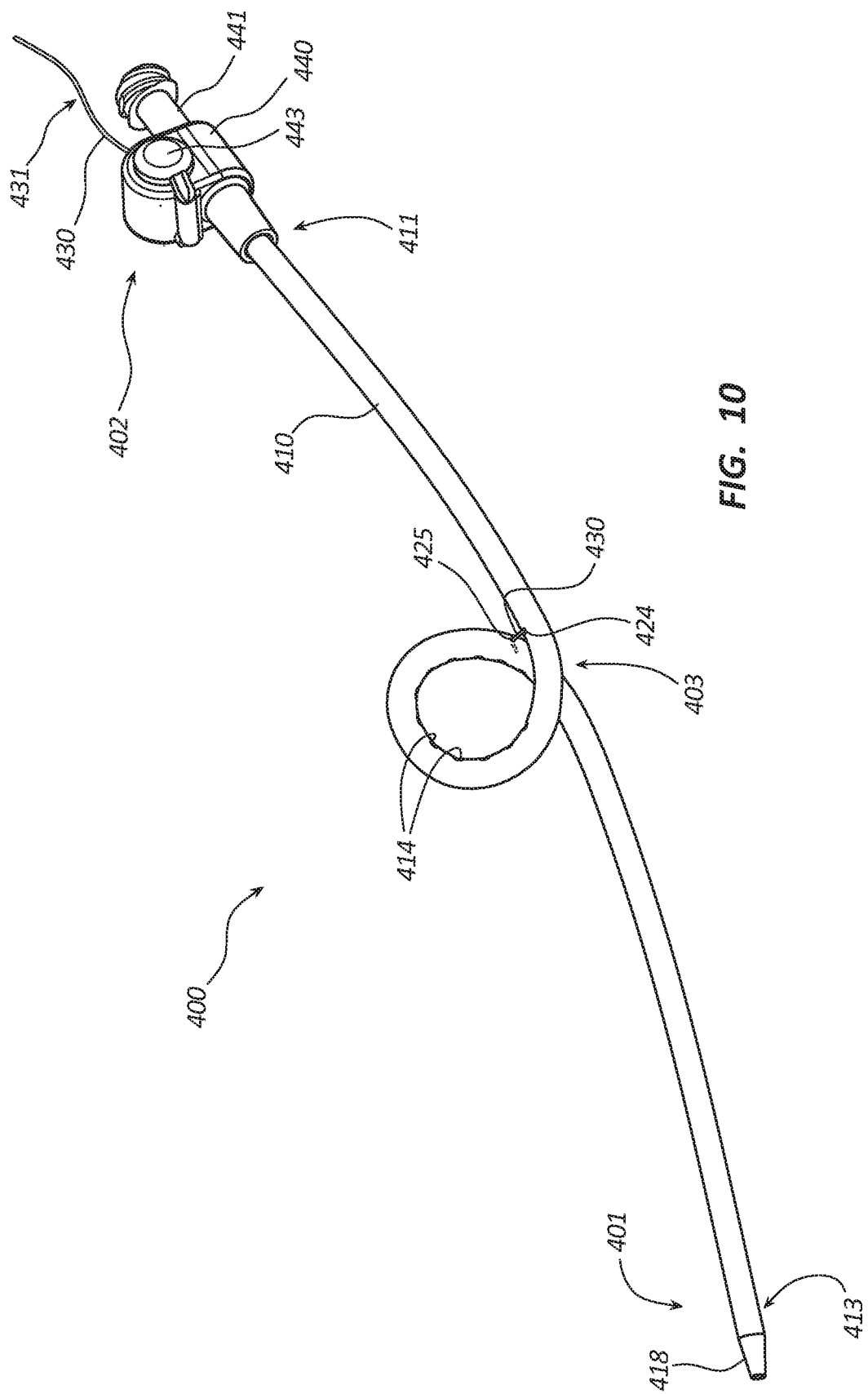
FIG. 10 is a perspective view of another embodiment of a drainage catheter in a second configuration.

FIG. 10 is a perspective view of a drainage catheter 400 in an anchor configuration. As with the drainage catheter 100 of FIGS. 1-7, the drainage catheter 400 of FIG. 10 may be disposed in a first or straight configuration (analogous to the straight configuration of the drainage catheter 100 as shown in FIG. 1) or in a second or anchor configuration such as shown in FIG. 10. As depicted, the drainage catheter 400 can include a catheter tube 410 having a distal end 413 and a proximal end 411, a catheter hub 440 coupled to the proximal end 411, and a suture 430 extending along the catheter tube 410 and extending proximally from the catheter hub 440. A distal tip 418 is shown coupled to the distal end 413. The suture 430 can be operably coupled to a middle portion 403 of the catheter tube 410 as previously described with a portion of the suture 430 extending externally of the tube 410 between an exit port 424 and an entrance port 425. In the anchor configuration, tension can be applied to the suture 430 causing a loop to be formed adjacent the middle portion 403 such that the distal portion 401 extends distally from the loop. Embodiments where the loop is disposed halfway between the proximal end 411 and the distal end 413 are within the scope of this disclosure as are embodiments wherein the loop is disposed closer to the proximal 411 than the distal end 413 and embodiment where the loop is disposed closer to the distal end 413 than the proximal end 411. The middle portion 403 can include a plurality of drainage ports 414. When the drainage catheter 400 is in the anchor configuration, the drainage ports 414 can be disposed adjacent the loop.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Changes may be made to the details of the above-described embodiments without departing from the underlying principles of the present disclosure.

The invention claimed is:

1. A drainage catheter comprising:
   a catheter tube comprising a drainage lumen disposed within the catheter tube and extending along a portion of the catheter tube, wherein a distal end of the catheter tube comprises an opening;
   a suture lumen disposed along a portion of the catheter tube, the suture lumen comprising a proximal region, a central region distal of the proximal region, a distal region distal of the central region, an exit port at a distal end of the proximal region, and an entrance port at a proximal end of the distal region; and
   a suture slidably disposed within the suture lumen along the proximal region, disposed through the exit port, disposed external to the suture lumen along the central region, disposed through the entrance port, and comprising an attachment segment disposed at a distal end of the suture that is fixedly attached to the catheter tube within the distal region of the suture lumen such that the suture lumen is compressed around the attachment segment, wherein the catheter tube is selectively curvable between the attachment segment and the exit port responsive to longitudinal displacement of the suture,
   wherein the suture lumen is disposed within an annular wall of the catheter tube, and
   wherein the suture lumen is not in communication with the drainage lumen.

2. The drainage catheter of claim 1, further comprising a catheter hub coupled to a proximal end of the catheter tube, the catheter hub comprising a suture passageway and a suture lock, the suture lock configured to selectively prevent and allow longitudinal displacement of the suture along the suture passageway,
   wherein in a secured configuration, the suture lock prevents longitudinal displacement of the suture through the suture passageway in a distal direction.

3. The drainage catheter of claim 1, wherein the entrance port and the exit port are disposed on the same side of the catheter tube in a straight configuration.

4. The drainage catheter of claim 1, further comprising a plurality of drainage ports disposed along the catheter tube.

5. The drainage catheter of claim 1, wherein, when disposed in an anchor configuration, a distal portion of the catheter tube comprises a first curved segment between the attachment segment and the exit port.

6. The drainage catheter of claim 5, wherein the catheter tube further comprises a distal tip and wherein the distal tip extends distally beyond the first curved segment.

7. The drainage catheter of claim 5, wherein the first curved segment is disposed adjacent a distal end of the catheter tube.

8. The drainage catheter of claim 5, wherein the catheter tube further comprises a second curve segment disposed adjacent a middle portion of the catheter tube.

9. The drainage catheter of claim 1, further comprising at least one radiopaque marker disposed along the catheter tube.

10. The drainage catheter of claim 1, wherein the attachment segment comprises an etched surface.

11. The drainage catheter of claim 1, wherein the attachment segment comprises a knot that is compressed by the suture lumen distal to the exit port.

12. The drainage catheter of claim 1, wherein the attachment segment comprises a bulbous portion that is compressed by the suture lumen distal to the exit port.

13. The drainage catheter of claim 1, wherein the annular wall comprises a protrusion extending inward along an inner surface of the annular wall that corresponds with the length of the suture lumen.

14. The drainage catheter of claim 1, wherein the drainage lumen comprises a D-shaped cross-section, wherein the suture lumen is disposed within the thicker portion of the annular wall.

* * * * *